(12) United States Patent
Szabo

(10) Patent No.: US 6,645,182 B1
(45) Date of Patent: *Nov. 11, 2003

(54) PIVOTABLE GUARD FOR SHIELDING A NEEDLE

(75) Inventor: Sandor Szabo, Elmwood Park, NJ (US)

(73) Assignee: Becton Dickinson and Company, Franklin Lakes, NJ (US)

(*) Notice: Subject to any disclaimer, the term of this patent is extended or adjusted under 35 U.S.C. 154(b) by 28 days.

This patent is subject to a terminal disclaimer.

(21) Appl. No.: 09/630,276

(22) Filed: Aug. 1, 2000

Related U.S. Application Data

(63) Continuation of application No. 08/925,974, filed on Sep. 9, 1997, now Pat. No. 6,120,482.

(51) Int. Cl.[7] ............................................. A61M 5/32
(52) U.S. Cl. ...................... 604/192; 604/198; 128/919
(58) Field of Search ............................. 604/181, 187, 604/110, 192, 198, 263, 208–210, 93.01; 206/364–365; 128/919

(56) References Cited

U.S. PATENT DOCUMENTS

| | | | |
|---|---|---|---|
| 2,559,474 A | 7/1951 | Son ............................ 128/215 |
| 2,739,591 A | 3/1956 | Yochem ...................... 128/218 |
| 3,658,061 A | 4/1972 | Hall .......................... 128/214.4 |
| 4,573,976 A | 3/1986 | Sampson et al. ............ 604/198 |
| 4,664,259 A * | 5/1987 | Landis ........................ 206/364 |
| 4,738,663 A | 4/1988 | Bogan ........................ 604/198 |
| 4,790,828 A | 12/1988 | Dombrowski et al. ...... 604/198 |
| 4,867,746 A | 9/1989 | Dufresne .................... 604/192 |
| 4,872,552 A | 10/1989 | Unger ........................ 206/365 |
| 4,883,469 A | 11/1989 | Glazier ....................... 604/192 |
| 4,886,503 A * | 12/1989 | Miller ........................ 604/192 |
| 4,892,521 A | 1/1990 | Laico et al. ................. 604/192 |
| 4,909,791 A | 3/1990 | Norelli ....................... 604/192 |
| 4,909,792 A * | 3/1990 | Norelli ....................... 604/192 |
| 4,915,696 A * | 4/1990 | Feimer ....................... 604/198 |
| 4,944,397 A * | 7/1990 | Miller ........................ 206/365 |
| 4,944,731 A | 7/1990 | Cole .......................... 604/192 |
| 4,950,249 A | 8/1990 | Jagger et al. ............... 604/192 |
| 4,976,699 A | 12/1990 | Gold .......................... 604/192 |
| 4,982,842 A | 1/1991 | Hollister .................... 206/365 |
| 4,994,046 A | 2/1991 | Wesson et al. ............. 604/198 |
| 5,011,475 A | 4/1991 | Olson ......................... 604/192 |
| 5,026,356 A * | 6/1991 | Smith ......................... 604/198 |
| 5,116,325 A * | 5/1992 | Paterson .................... 604/192 |
| 5,135,509 A | 8/1992 | Olliffe ........................ 604/192 |
| 5,139,489 A | 8/1992 | Hollister .................... 604/192 |
| 5,151,089 A | 9/1992 | Kirk, III et al. ............ 604/192 |
| 5,152,751 A * | 10/1992 | Kozlowski ................. 604/263 |
| 5,188,611 A * | 2/1993 | Orgain ....................... 604/192 |
| 5,207,653 A | 5/1993 | Janjua et al. ............... 604/192 |
| 5,215,534 A | 6/1993 | De Harde et al. .......... 604/198 |
| 5,232,454 A | 8/1993 | Hollister .................... 604/192 |
| 5,232,455 A | 8/1993 | Hollister .................... 604/192 |
| 5,242,417 A | 9/1993 | Paudler ...................... 604/192 |

(List continued on next page.)

Primary Examiner—Brian L. Casler
Assistant Examiner—Mark K Han
(74) Attorney, Agent, or Firm—Jeanne P. Lukasavage; John L. Voellmicke

(57) ABSTRACT

A needle guard assembly is provided for mounting to the hub of a needle assembly. The needle guard assembly includes a guide that is engageable on the hub. An elongate U-shaped cover is hingedly mounted to the guide and can be rotated from a first position where the needle cannula is substantially surrounded by the U-shaped walls of the cover into a second position where the needle cannula is exposed for use. The needle guard assembly further includes a slide that is slidably engaged in the guide and movable from a first position where the slide cooperatively engages the cover for completely surrounding the needle cannula to a second position where the slide is spaced proximally from the cover, thereby permitting the cover to rotate into its second position.

12 Claims, 4 Drawing Sheets

U.S. PATENT DOCUMENTS

| | | | | |
|---|---|---|---|---|
| 5,290,264 A | * | 3/1994 | Utterberg | 604/263 |
| 5,312,369 A | | 5/1994 | Arcusin et al. | 604/192 |
| 5,348,544 A | * | 9/1994 | Sweeney et al. | 604/198 |
| 5,405,332 A | * | 4/1995 | Opalek | 604/192 |
| 5,445,619 A | * | 8/1995 | Burns | 604/263 |
| 5,466,223 A | * | 11/1995 | Bressler et al. | 604/263 |
| 5,486,163 A | | 1/1996 | Haynes | 604/192 |
| 5,490,841 A | | 2/1996 | Landis | 604/110 |
| 5,509,907 A | | 4/1996 | Bevilacqua | 604/263 |
| 5,672,161 A | * | 9/1997 | Allen et al. | 604/263 |
| 5,702,369 A | * | 12/1997 | Mercereau | 604/263 |
| 5,807,351 A | * | 9/1998 | Kashmer | 604/192 |
| 5,868,716 A | * | 2/1999 | Sweeney et al. | 604/192 |
| 6,120,482 A | * | 9/2000 | Szabo | 128/919 |

* cited by examiner

PIVOTABLE GUARD FOR SHIELDING A NEEDLE

This application of a continuation of application Ser. No. 08/925,974 filed Sep. 9, 1997 now U.S. Pat. No. 6,120,482.

BACKGROUND OF THE INVENTION

1. Field of the Invention

The subject invention relates to a needle guard for enclosing and protecting a needle cannula to avoid accidental sticks and to prevent contamination of the needle cannula prior to use.

2. Description of the Prior Art

A prior art needle cannula is a long narrow metal tube having opposed proximal and distal ends and having a lumen extending between the ends. The distal end of the prior art needle cannula typically is beveled to define a pointed cutting edge that is sufficiently sharp to pierce the skin of a patient or to penetrate a piercable membrane that seals a container of medicine. The proximal end of the needle cannula typically is secured to a structure that will enable fluid communication through the lumen. For example, some prior art needle cannulas are rigidly and permanently connected to the distal end of a hypodermic syringe barrel. Other prior art needle cannulas are securely mounted to a hubs which in turn can be threadedly engaged with the distal end of a prior art syringe barrels.

It is well known that needle cannulas are capable of transmitting disease or infection. For example, an accidental stick with a used needle cannula can transmit disease from the patient on whom the needle cannula had been used. An accidental stick with an unused needle cannula can leave an open wound that is subject to infection if not treated properly. Infection or disease also can be transmitted by means other than an accidental stick. For example contact with an intermediate portion of a needle cannula prior to use can impart contaminants to the outer surface of the needle cannula. These contaminants may be transferred to the patient when the needle cannula is used. Similarly, contact with a side wall region of a used needle cannula can possibly result in a transfer of infectious bodily fluids.

Most needle cannulas are provided with guards or shields that are intended to prevent accidental needle contact. Some needle shields include an elongate rigid shield having an open proximal end and a closed distal end. The shield is mounted over the needle cannula in a distal-to-proximal direction and is frictionally retained on the needle hub or on distal regions of a syringe barrel. The shield can be removed immediately prior to use by exerting a distally directed force on the shield relative to the needle cannula. Shields of this type are very effective and are commonly used for avoiding needle sticks prior to the initial use of a needle cannula. However, it is generally recommended not to use this type of shield after injection because of the possibility of needle sticks during the reshielding process.

Some prior art needle cannulas are provided with a hinged guard. The prior art hinged needle guard may define a generally U-shaped channel having a proximal end that is hingedly articulated to or near the needle hub. The needle guard may be rotated from a first position where the needle cannula is exposed for use to a second position where the needle cannula is partly surrounded by the needle guard. Prior art hinged needle guards are effective for preventing accidental needle sticks. Additionally, prior art needle guards substantially reduce the possibility of inadvertent contact with side wall regions of the needle cannula. However, one longitudinal side of the needle cannula is left exposed by the prior art hinged needle guard. Thus, environmental materials may be able to contact this needle cannula before the initial use.

The prior art hinged needle guard typically will prevent inadvertent contact with any portion of the needle cannula after use. However, the long thin needle cannulas can be bent during use or by inadvertent contact with a hard surface immediately after use. In these situations, the portions of the bent needle cannula may project from the open side of the prior art hinged needle guards. The greatest deviation from a perfect axial alignment is likely to be at the distal tip of the bent needle cannula. Thus, the pointed distal tip could be exposed from the prior art hinged needle guard and could accidentally stick a health care worker who reasonably assumed that the needle was safely enclosed within the prior art hinged guard.

SUMMARY OF THE INVENTION

The subject invention is directed to a needle guard assembly for use with a needle cannula. The needle cannula may be of prior art construction, and includes proximal and distal ends. A lumen extends continuously between the proximal and distal ends for accommodating a flow of fluid. The distal end of the needle cannula may be beveled to define a point. The proximal end of the needle cannula may be mounted to structure for enabling fluid flow through the lumen. In a preferred embodiment, as described and illustrated herein, the proximal end of the needle cannula is securely connected to a needle hub. The needle hub may include structure for releasable attachment to a medical implement, such as a hypodermic syringe barrel. In other embodiments, the needle cannula may be mounted directly in a medical implement, such as a hypodermic syringe barrel.

The needle guard assembly of the subject invention includes a guide, a cover and a slide. The guide is securely attachable near the proximal end of the needle cannula. The guide may include a channel for receiving the slide of the needle guard assembly, as explained below.

The cover of the needle guard assembly is an elongate substantially rigid structure having a proximal end and a closed distal end. The cover defines a length that preferably equals or exceeds the length of the needle cannula. Portions of the cover between the proximal and distal ends are of generally U-shaped cross section and are configured to receive the needle cannula therein. The U-shaped portions of the cover may have grooves or similar structure for receiving the slide of the needle guard assembly, as explained below. The proximal end of the cover is joined to the guide at a hinge. The hinge may define a unitary connection between the guide and the cover. However the guide and the cover preferably are separate members that are joined at the hinge. The hinge enables the cover to be hingedly rotated relative to the guide between a first position where the needle cannula is safely received within the U-shaped portions of the cover and a second position where the needle cannula is exposed for use.

The slide of the needle guard assembly is slidably engaged in the channel of the guide for movement between a first position where the slide is adjacent the needle cannula and a second position where the slide is spaced proximally of the needle cannula. The slide may be slidably receivable within the grooves of the cover when the cover is in its first position. Thus, the needle cannula can be completely enclosed between the cover and the slide.

Retaining means may be provided for preventing unintended movement of the slide relative to the guide and/or the cover.

The cover and the slide initially may be in their first positions relative to the guide for enclosing the needle cannula. These relative positions of the cover and slide help protect the needle cannula from contamination prior to use. The needle cannula is placed in condition for use by moving the slide proximally relative to both the guide and the cover and into the second position of the slide. Once the slide has reached its second position, the cover may be rotated away from the needle cannula and into its second position. The needle cannula then may be used in the conventional manner. After use, a thumb or forefinger is used to rotate the cover back to its first position relative to the guide and into substantially surrounding relationship to the used needle cannula. The health care worker then exerts forces on the proximal end of the slide with a thumb or forefinger to urge the slide distally toward its first position. The slide will slidably advance through the channel of the guide and will engage in the grooves of the cover. This distal advancement of the slide in the cover prevents rotation of the cover and simultaneously encloses the one side of the needle cannula that had been left exposed by the U-shaped wall of the cover. Sufficient distal advancement of the slide will completely enclose the cover. Locking structure may be provided for irreversibly maintaining the slide at its distal extreme position to prevent an unauthorized re-exposure of the used needle cannula.

DETAILED DESCRIPTION OF THE PREFERRED EMBODIMENT

Figure 1:
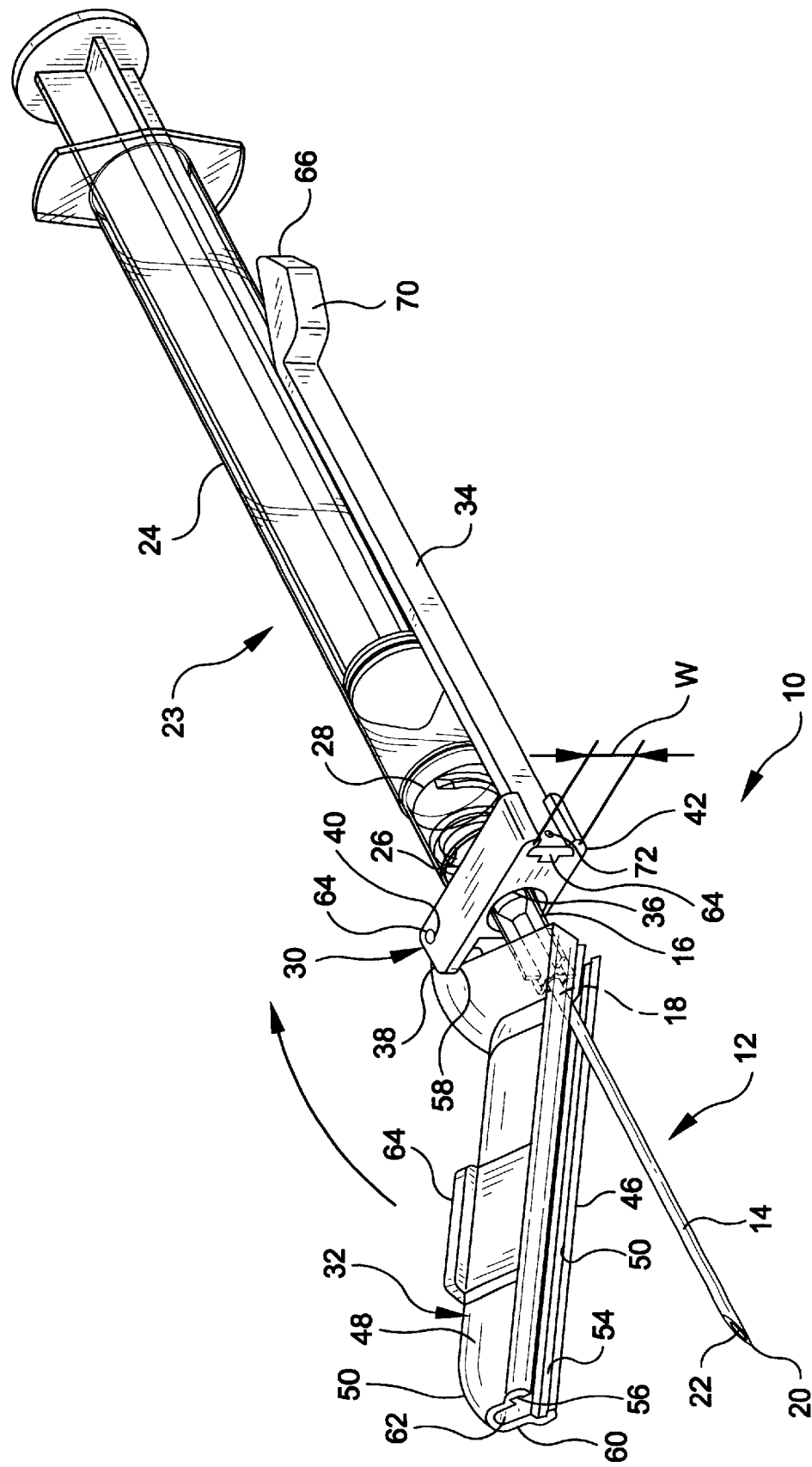
FIG. 1 is a perspective view of a needle guard assembly in a partly opened condition with the needle cannula being exposed.

A needle guard assembly in accordance with the subject invention is identified generally by the numeral 10 in FIG. 1. Needle guard assembly 10 is used with a needle assembly 12 which comprises a needle cannula 14 and a needle hub 16. Needle cannula 14 has a proximal end 18, that is securely attached to the needle hub, and a distal end 20 that is beveled to define a sharp tip. A lumen 22 extends between proximal and distal ends 18 and 20 for permitting fluid flow through needle cannula 14.

Needle guard assembly 10 and needle assembly 12 can be used with a prior art hypodermic syringe 23 having a barrel 24. Syringe barrel 24 includes a proximal end (not shown) and a distal end 26 defining a luer collar 28. Needle hub 16 is releasably threaded with luer collar 28 in a conventional manner.

Needle guard assembly 10 includes, a guide 30, a cover 32 and a slide 34. Guide 30 is preferably unitarily molded from a thermoplastic material and includes a mounting aperture 36 dimensioned and configured for engagement on needle hub 16. Guide 30 further includes a pair of substantially parallel support walls 38 defining planes on opposite respective sides of mounting aperture 36. Support walls 38 have coaxial hinge apertures 40 extending therethrough and aligned transversely with mounting aperture 36.

In this preferred embodiment the guide is mounted directly to the needle hub. It is also within the purview of the present invention to mount the guide on the needle cannula or on the hub and the needle cannula. Also, the guide can be mounted on the distal end of a syringe barrel. Some syringe barrels are provided with a distal tip which contains a permanently attached needle cannula. With these syringes, the guide can be attached directly to the distal tip.

Figure 4:
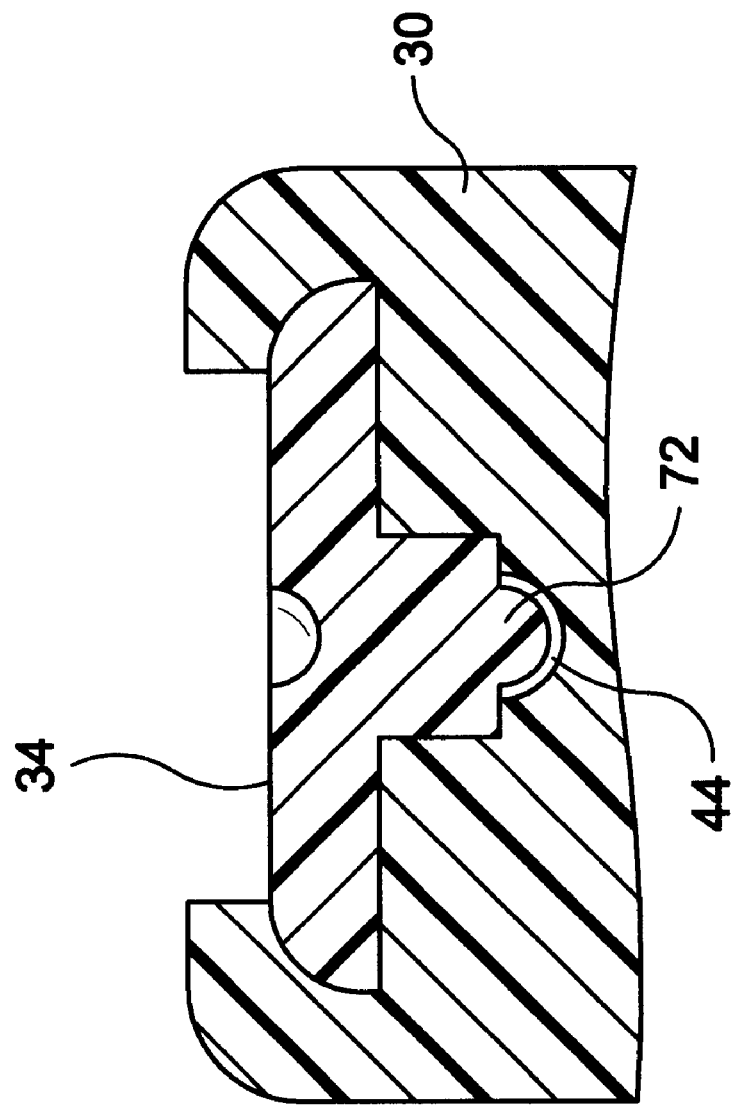
FIG. 4 is a cross-sectional view of portions of the guide and the slide taken along line 4—4 in FIG. 2.

Guide 30 further preferably includes a grooved channel 42 which extends substantially parallel to mounting aperture 36. Channel 42 defines a width "W" as shown in FIG. 1, and is disposed such that mounting aperture 36 is between channel 42 and support walls 38. A locking recess 44 is formed in portions of guide 30 defining channel 42 as illustrated in FIG. 4.

Figure 2:
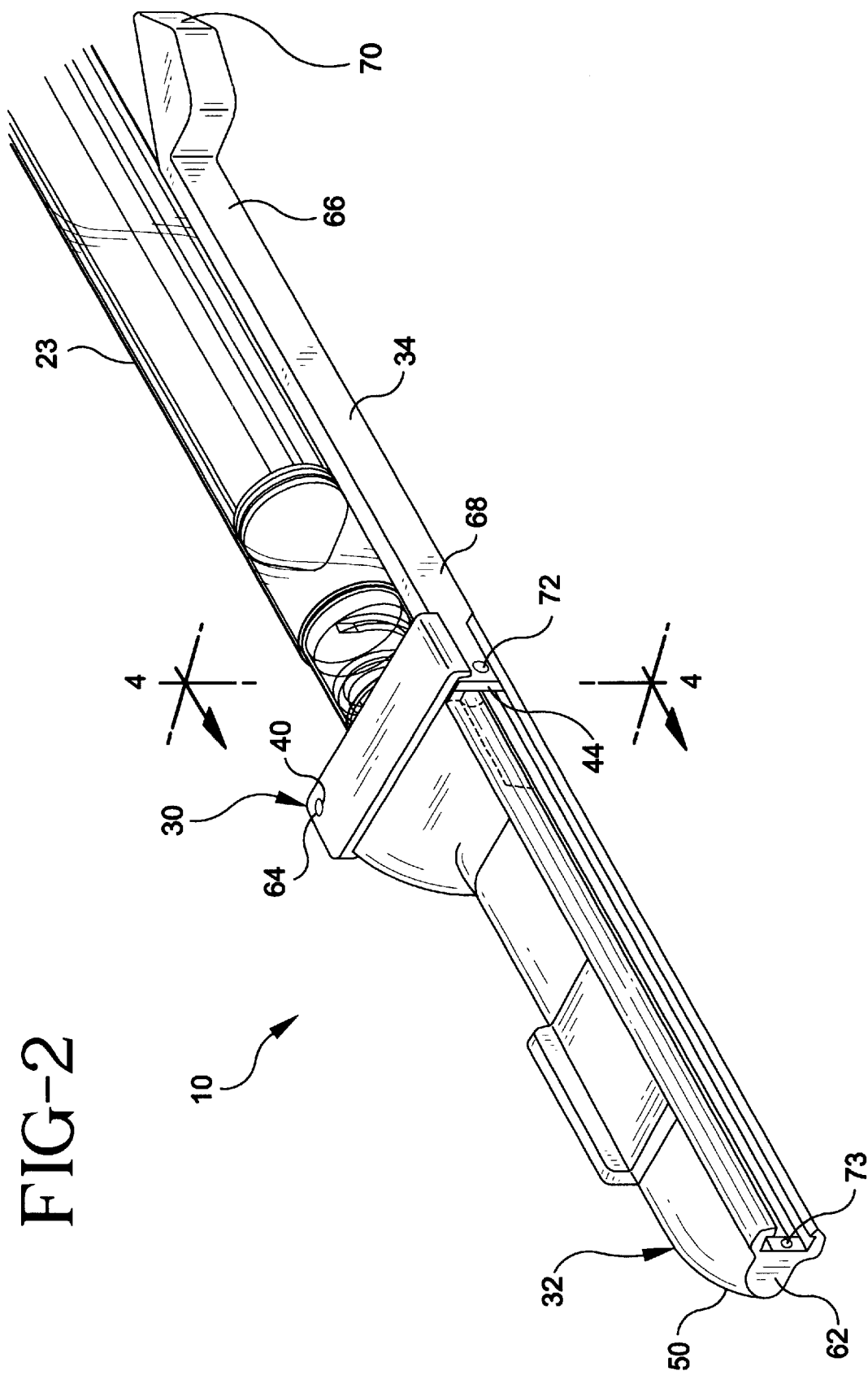
FIG. 2 is a perspective view with the cover disposed in its partly shielding position.
Figure 3:
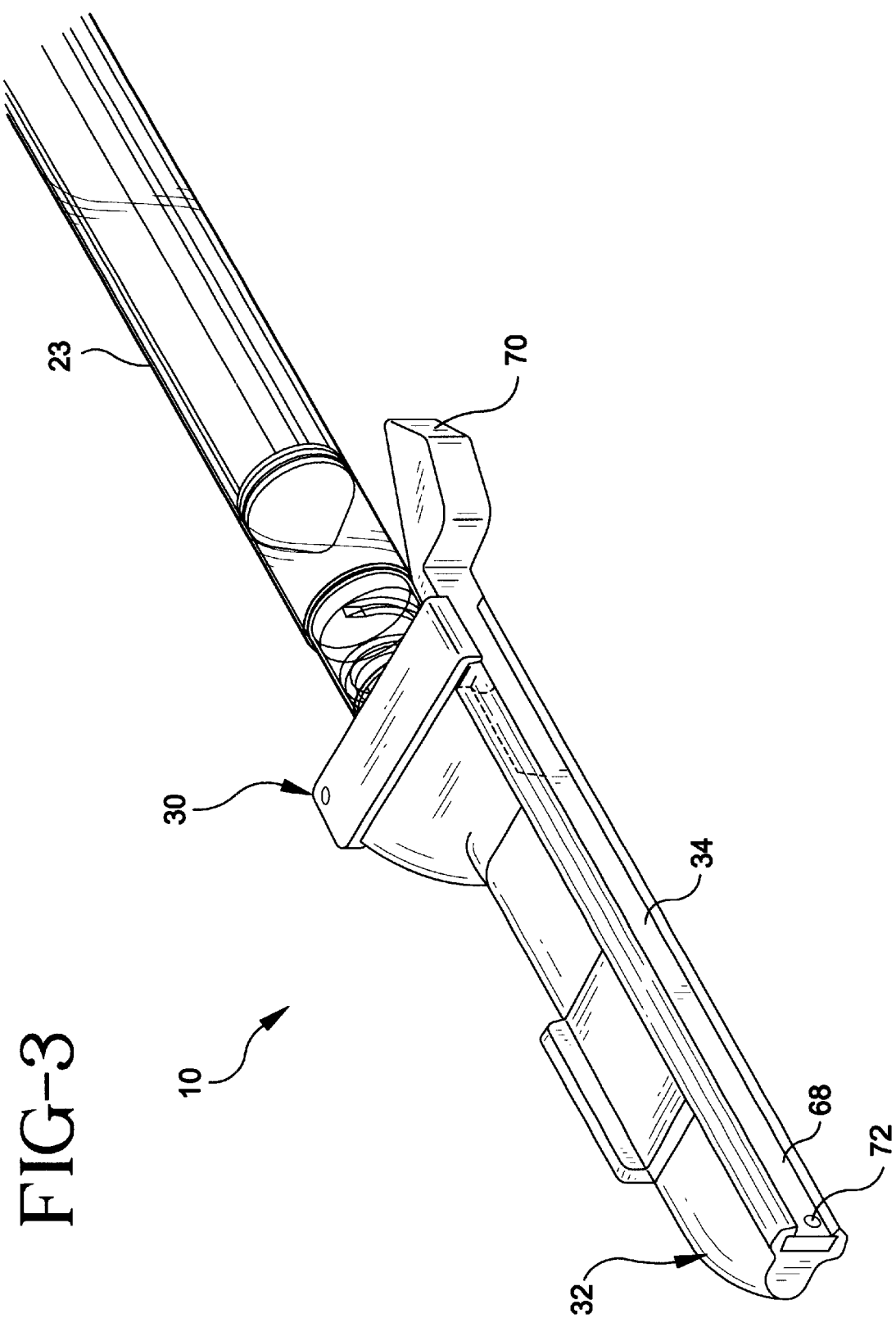
FIG. 3 is a perspective view showing the slide in a distal extreme position where the needle cannula is safely completely enclosed between the cover and the slide.

Cover 32 is preferably an elongate U-shaped structure having parallel spaced-apart side walls 46 and 48 and a connecting wall 50. Side walls 46 and 48 are spaced from one another by a distance greater than the width of needle cannula 14 and define.-a length sufficient to accept the needle cannula 14. Grooves 54 and 56 are formed in inwardly facing surfaces of side walls 46 and 48. Opposed grooves 54 and 56 define an internal width for U-shaped cover 32 substantially equal to the width "W" for channel 42 in guide 30. Cover 32 includes a proximal end 58 and a distal end 60. Proximal end 58 of cover 32 is open. Distal end 60 of cover 32 preferably includes a distal end wall 62 that extends across connecting wall 50 and at least portions of side walls 46 and 48. Proximal end 58 of cover 32 includes a pair of coaxial hinge pins 64 that are L rotatably received in hinge apertures 40. Thus, cover 32 can be rotated relative to guide 30 from a first position where needle cannula 14 is within U-shaped cover 32, as illustrated in FIG. 2, to a second position where cover 32 is angularly offset from needle cannula 14. Portions of cover 32 between proximal and distal ends 58 and 60 preferably include a thumb actuator 64 dimensioned for receiving digitally directed forces thereon.

Slide 34 is an elongate rigid narrow rectangular structure having opposed proximal and distal ends 66 and 68 respectively. Proximal end 66 of slide 34 defines an actuator 70 that is dimensioned and configured for receiving digitally directed forces thereon in either the proximal or distal directions. Portions of slide 34 distally of the actuator thereof are cross-sectionally configured for slidable receipt in channel 42 of guide 30. Portions of slide 34 in proximity to distal end 68 include a locking detent 72 dimensioned for releasable engagement in locking recess 44 of guide 30 as illustrated in FIG. 4.

Guard assembly 10 is initially assembled by snapping hinge pins 64 of cover 32 into hinge apertures 40 of guide 30. Assembly may proceed by slidably inserting distal end 68 of slide 34 into channel 42 of guide 30 such that locking detent 72 is releasably engaged in recess 44 of guide 30. Needle assembly 12 then is advanced slidably through mounting aperture 36 of guide 30, such that portions of guide 30 adjacent mounting aperture 36 lock into needle hub 16. Cover 32 then is pivoted to its first position substantially surrounding needle cannula 14 as shown in FIG. 2. In this first position, the entirety of needle cannula 14, including sharply pointed distal tip 20 thereof, is safely disposed in U-shaped cover 32. However, an elongate side opening of cover 32 between side walls 46 and 48 leaves intermediate portions of needle cannula 14 exposed.

Slide 34 then is moved distally through channel 42 of guide 30 and into the opposed grooves 54 and 56. Sufficient advancement of slide 34 in a distal direction will cause locking detent 72 to engage recess 73 in distal end wall 62 of cover 32. Sufficient force on proximal end 66 of slide 34 will cause a minor deflection of cover 32 and slide 34 such that locking detent 72 of slide 34 is releasably engaged with end wall 62 of cover 32. In this condition, needle cannula 14 is safely enclosed between cover 32 and slide 34 of needle guard assembly 10.

In this preferred embodiment, locking means are provided. Specifically in accord with one implementation of the invention, the slide is releasably lockable in its second slide position with respect to the guide by interaction between locking detent 72 on the slide and recess 44 in the guide. Also, the slide is releasably lockable in its first slide position through interaction of locking detent 72 on the slide and recess 73 in the cover. This structure is merely preferred. It is within the purview of the present invention to include on any combination of projections and recesses in the slide which interact with any combination of projections and recesses in the guide or cover. The structure taught herein is merely representative of these many possibilities. Also, the components can be shaped so that the slide is releasably retained in either position through frictional action such as by dimensioning portions of the guide and slide or the guide and the cover such that at the first and second positions the slide meets with increased resistance to motion thereby releasably retaining the slide in selected positions.

Hypodermic syringe 23 can be used by merely exerting proximally directed forces on actuator 70 of slide 34 to move slide 34 into the orientation, illustrated in FIG. 2. Digitally directed forces then are exerted on actuator 64 to cause cover 32 to rotate away from needle cannula 14 and in the direction indicated by arrow A in FIG. 1. Hypodermic syringe 24 and needle assembly 12 then can be used in the conventional manner.

After use, the health care technician employing hypodermic syringe 24 exerts digital forces on actuator 64 of cover 32, such that cover 32 pivots in a direction opposite from arrow A in FIG. 1 and into substantially surrounding relationship to used needle cannula 14. The technician then exerts a distally directed force on actuator 70 at proximal end 66 of slide 34, such that slide 34 moves distally through channel 44 in guide 30 and into grooves 54 and 56 of cover 32. Any misalignment of needle cannula 14 that may have occurred during use will be corrected as slide 34 moves distally relative to cover 32. More particularly, slide 34 will realign needle cannula 14, and urge needle cannula 14 fully into the U-shaped channel of cover 32. Sufficient axial advancement of slide 34 will cause detent 72 to lock with distal end wall 62 of cover 32.

What is claimed is:

1. A needle guard assembly for protectively enclosing a needle cannula comprising:
   a needle cannula having a proximal end and a sharp distal end;
   a guide securely attached in proximity to said proximal end of said needle cannula;
   a cover hingedly connected to said guide for pivoting between a first cover position where said needle cannula is at least partly enclosed by said cover and a second cover position where said needle cannula is exposed for use; and
   a slide slidably engaged with said guide for movement between a first slide position where said guide is slidably engaged with said cover when said cover is in said first cover position, such that said slide and said cover surround said needle cannula and a second slide position where said slide is spaced from said cover.

2. The needle guard assembly of claim 1, wherein either said guide or said cover includes a pair of coaxial pivot pins hingedly connected in apertures formed in the other of said guide or said cover for said cover to pivot between said first cover position and said second cover position.

3. The needle guard assembly of claim 1, wherein said guide includes a grooved channel extending therethrough and having a width for slidably receiving said slide.

4. The needle guard assembly of claim 3, wherein said slide includes locking means for releasably retaining said slide in said first slide position.

5. The needle guard assembly of claim 3, wherein said cover is substantially U-shaped and includes first and second spaced apart side walls and a connecting wall extending between said side walls, said side walls being formed with grooves in opposed facing positions thereon, the grooves defining a width substantially equal to the width of the channel in said guide, said grooves being disposed to substantially align with said channel when said cover is rotated into said first cover position.

6. The needle guard assembly of claim 3, wherein said slide includes. locking means for releasably locking said slide in said second slide position.

7. The needle guard assembly of claim 1, wherein said proximal end of said needle cannula is securely embedded in a needle hub, said needle hub having means for threaded connection to a hypodermic syringe, said guide including a mounting aperture extending therethrough, said mounting aperture being dimensioned and configured to enable secure mounting of said guide to said needle hub.

8. The needle guard assembly of claim 1, wherein said cover includes an actuator dimensioned and disposed for rotating said cover between said first cover position and said second cover position.

9. The needle guard assembly of claim 1, wherein said slide includes an actuator adjacent said proximal end, said actuator being configured for facilitating digital manipulation of said slide between said first slide position and said second slide position.

10. A needle guard assembly for protectively enclosing a needle cannula including: p1 a guide having a channel; p1 a cover with a side opening mounted to the guide for pivoting movement between a first position in which the needle cannula is exposed for use and a second position in which the needle cannula is at least partially enclosed by the cover and partially exposed through the side opening; and p1 a slide slidably engaged to the channel of the guide and movable between a first position in which the slide is disposed in the side opening and a second position in which the slide is not in the side opening.

11. The needle guard assembly of claim 10 further comprising a detent for locking the slide in the first position.

12. The needle guard assembly of claim 10 further comprising a detent for locking the slide in the second position.

* * * * *